US00PP12199P2

(12) United States Plant Patent
Hoy, Jr.

(10) Patent No.: US PP12,199 P2
(45) Date of Patent: Nov. 13, 2001

(54) HYBRID TEA ROSE PLANT NAMED 'HILMOC'

(75) Inventor: Lowell L. Hoy, Jr., Richmond, IN (US)

(73) Assignee: E. G. Hill Company, Inc., Richmond, IN (US)

( * ) Notice: Subject to any disclaimer, the term of this patent is extended or adjusted under 35 U.S.C. 154(b) by 0 days.

(21) Appl. No.: 09/399,207

(22) Filed: Sep. 17, 1999

(51) Int. Cl.[7] ..... A01H 5/00
(52) U.S. Cl. ..... Plt./140
(58) Field of Search ..... Plt./140, 139

*Primary Examiner*—Bruce R. Campell
*Assistant Examiner*—June Hwu
(74) *Attorney, Agent, or Firm*—Christie, Parker & Hale, LLP

(57) ABSTRACT

Described is a hybrid tea rose plant variety producing red flowers of good form.

1 Drawing Sheet

BACKGROUND OF THE INVENTION

The present invention relates to a new and distinct hybrid tea rose variety which was originated by my crossing as seed parent the variety known as 'Cindy' (patented MEltinor, U.S. Plant Pat. No. 3,910) and as pollen parent the variety known as 'Samantha' (patented JACmantha, U.S. Plant Pat. No. 3,727). The varietal denomination of this new rose is 'Hilmoc'.

SUMMARY OF THE INVENTION

Among the novel characteristics possessed by the new variety which distinguish it from all other red rose varieties of which I am aware are its long vase life and long stems. Asexual reproduction by budding/grafting of the new variety as performed in Richmond, Ind., shows that the foregoing and other distinguishing characteristics come true to form and are established and transmitted through succeeding propagation. Other known forms of asexual reproduction may be also used.

COMPARISON WITH PARENTS

This variety is different and distinguishes from its pollen parent 'Samantha' and seed-parent 'Cindy' by having greater vase life and stem length than 'Samantha' while retaining its vivid red color and possessing the high production of its seed parent 'Cindy'.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

The following is a detailed description of the new variety, from two year old plants grown under glass in Richmond, Ind., in the month of July. Plant height at the time of testing was about 4½ feet high by about 18' wide. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

Fragrance: None.

Bud:

*Peduncle.*—Medium length (about 4"–5"), medium diameter, and medium strength, with smooth bark.
*Color.*—Near 146A.
*Thorns.*—None.
*Prickles.*—None.
*Hair.*—Few.
*Color of hairs.*—Near 157A.

Before calyx breaks:

*Bud size.*—Small, length about 1¾", width about 1½", diameter about ½–1".
*Bud form.*—Short pointed without a conspicuous neck; with foliaceous appendages on the surface of the bud, with slender foliaceous parts extending beyond the tip of the bud equal to ½ or more its length. As it opens the petal arrangement is imbricated.
*Color of calyx.*—Near 138B.
*As calyx breaks.*—Inside color: near 138D bordered with near 138B.
*As first petal breaks.*—Outside color near 138A bordered near 138B.
*Bud size.*—Small, length about 1¾", width about 1½". Bud form: Short, pointed. Texture of Calyx: Smooth upper and lower sides.
*Color petal outside.*—Near 60A.
*Inside.*—Near 53A.
*Bud opening in greenhouse.*—Opens well.

Flower:

*Flowers borne.*—Singly and in clusters of about 2 or 3 blooms (about 32"–35") on long medium strong stems.

Bloom (open):

*Size when fully open.*—Medium large, about 5 inches to about 5½ inches.
*Petalage.*—Double, 24–27.
*Form.*—High centered, becoming flat upon opening, petals loosely roll outward at maturity and are imbricated.
*Petals.*—Thick, inside velvety, outside satiny.
*Petals/shape.*—Round, apex obtuse, length about 1¾", width about 2".

*Color of outer petal.*—Outside surface: Near 60B. Inside surface: Near 53A.

*Color of intermediate petal.*—Outside surface: Near 60B. Inside surface: Near 53A.

*Color of inner petal.*—Outside surface: Near 60B. Inside surface: Near 53A.

*Behavior of petals in greenhouse.*—Persist.

*Flower longevity.*—About 14 days after cutting.

*Color of open bloom.*—Near 53A.

*Color three days open.*—Near 53A.

Foliage:

*Leaves.*—Compound of three to five leaflets, medium size, length about 2⅛", width about 1¾".

*Arrangement.*—Leathery texture on upper and lower surfaces: arranged in an alternating fashion along the stem.

*Leaflets.*—Shape: Elliptical. Apex: Acute. Base: Acute. Margin: Simply serrate.

*Color of leaflets.*—Mature, upper surface: Near 137A. Mature, under surface: Near 191A. Young, upper surface: Near 187A. Young, under surface: Near 183C. Upper side: Smooth. Under side: Sparsely thorny.

*Stipules.*—Medium length about ½", medium width about ¼", with points which are medium length turning out an angle of more than 45°. Texture is smooth on upper and lower sides.

*Sepals.*—Permanent, medium length (about 2"), spear-shaped, recurved width at base about ½" tip about 1/16".

*Under side.*—Near 138D bordered with near 138B.

*Upper side.*—Near 138A bordered with near 138B.

Growth:

*Habit.*—Upright, branching.

*Growth.*—Free, vigorous.

*Canes.*—Medium diameter about ¾", length about 32–35".

*Main stems.*—Near 138A.

*Thorns.*—Several, medium length about ⅜", slightly hooked downward, with broad narrow base.

*Color of thorns.*—Near 165B.

*Prickles.*—Very few.

*Color of prickles.*—Near 138A.

*Hairs.*—None.

*Texture of bark.*—Smooth.

*Branches.*—Near 137C.

*Thorns.*—Several, medium length about ⅜", straight, downward, with broad, narrow base.

*Color of thorns.*—Near 144B.

*Prickles.*—None.

*Hairs.*—None.

*New shoots.*—Color: Near 138B. Thorns: Several, medium length about ¼" with broad, narrow base.

*Color of thorns.*—Tip: Near 143D. Base: Near 39A. Prickles: None. Hairs: None. Texture of Bark: Smooth.

Reproductive organs:

*Stamens.*—Medium about ½", about 98, arranged regularly, tucked in calyx.

*Filaments.*—Short about ¼" most with anthers.

*Color of filaments.*—Near 51A.

*Anthers.*—Medium about 3/16", all open at once, about 98 anthers.

*Color of anthers.*—Margins near 163C. Center near 39A.

*Pollen.*—Moderate.

*Color of pollen.*—Near 160B.

*Quantity pistils.*—Many about 160, length about ⅜".

*Styles.*—Even, short, about ¼", moderately thin, bunched.

*Color of styles.*—Near 53B.

*Color of stigma.*—Near 158B.

*Ovules.*—All encased.

*Hips.*—None.

*Seeds.*—None.

I claim:

1. A new and distinct hybrid tea rose plant known of the variety known as 'HILMOC' substantially as shown and described.

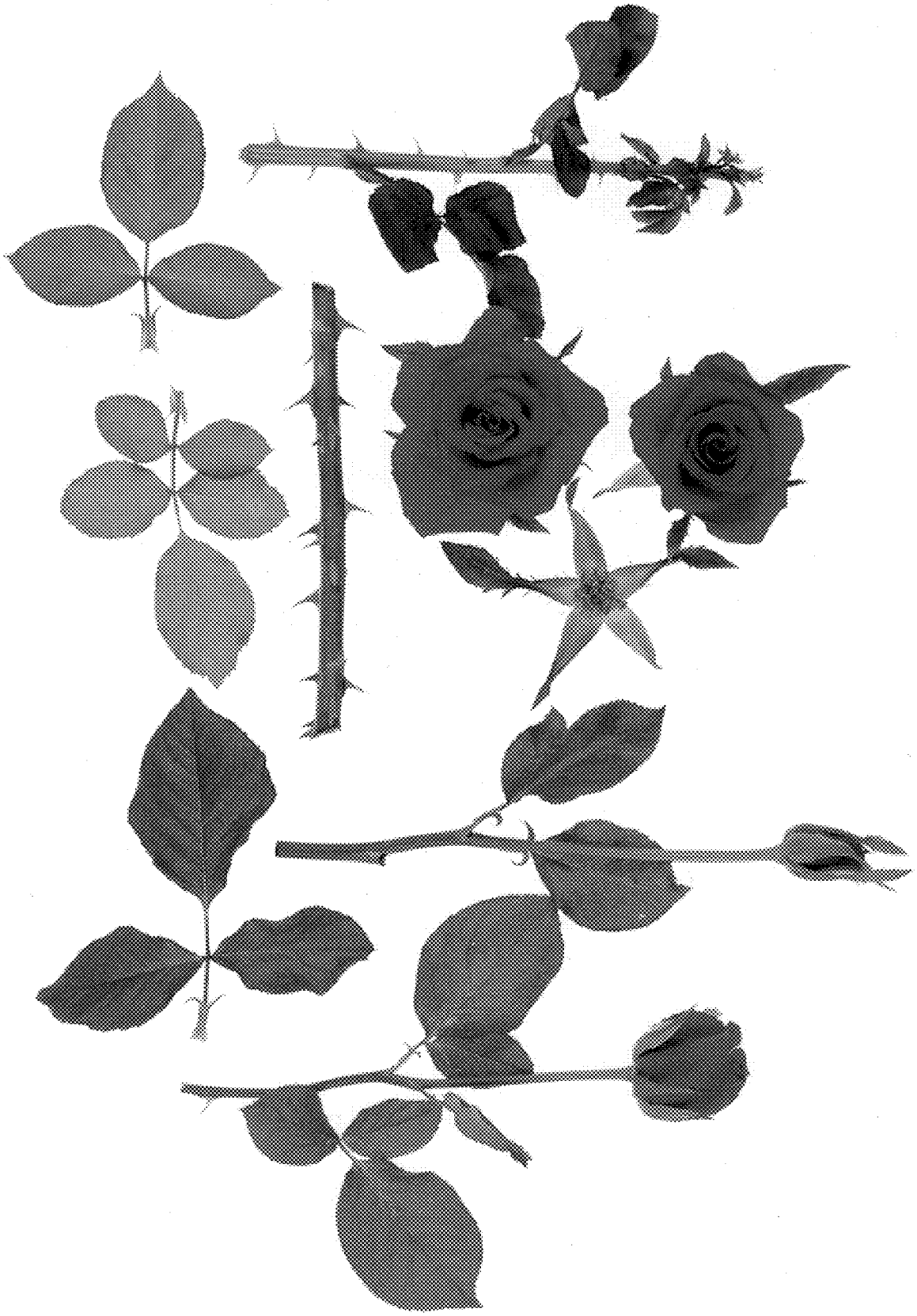

* * * * *